US00PP34940P2

(12) United States Plant Patent
Star

(10) Patent No.: US PP34,940 P2
(45) Date of Patent: Jan. 24, 2023

(54) ***SANGUISORBA* PLANT NAMED 'TOUGH DREAM'**

(50) Latin Name: *Sanguisorba officinalis*
Varietal Denomination: Tough Dream

(71) Applicant: Jan Star, Rijnsburg (NL)

(72) Inventor: Jan Star, Rijnsburg (NL)

( * ) Notice: Subject to any disclaimer, the term of this patent is extended or adjusted under 35 U.S.C. 154(b) by 0 days.

(21) Appl. No.: 17/752,844

(22) Filed: May 24, 2022

(30) Foreign Application Priority Data

Nov. 1, 2021 (QZ) ..... PBR20212735

(51) Int. Cl.
*A01H 6/74* (2018.01)
*A01H 5/02* (2018.01)

(52) U.S. Cl.
USPC ..... Plt./263.1

(58) Field of Classification Search
USPC ..... Plt./263.1
See application file for complete search history.

*Primary Examiner* — Annette H Para
(74) *Attorney, Agent, or Firm* — Penny J. Aguirre

(57) ABSTRACT

The new cultivar of *Sanguisorba* plant named 'Tough Dream' that is characterized by its strong branches, its exhibits inflorescences and flowers that are small in size and deep burgundy-red in color, and its sturdy and upright flowers.

2 Drawing Sheets

Botanical classification: *Sanguisorba officinalis*.
Variety denomination: 'Tough Dream'.

CROSS REFERENCE TO A RELATED APPLICATIONS

This application claims priority to European Community Plant Variety Office (CPVO) Plant Breeder's Rights Application No. 2021/2735 filed on Nov. 1, 2021, application No. 2021/2735, under 35 U.S.C. 119(f), the entire contents of which is incorporated by reference herein. This application is also related to U.S. Plant Patent Application filed for a plant derived from the same breeding program that is entitled *Sanguisorba* Plant Named 'Red Dream' (U.S. Plant Pat. No. 32,441) and *Sanguisorba* Plant Named 'Big Dream' (U.S. Plant Pat. No. 33,601). This application is co-pending with U.S. Plant Patent Applications filed for plants derived from the same breeding program that are entitled *Sanguisorba* Plant Named 'Fall Dream' (U.S. Plant patent application Ser. No. 17/752,837), *Sanguisorba* Plant Named 'Sweet Dream' (U.S. Plant patent application Ser. No. 17/752,840).

BACKGROUND OF THE INVENTION

The present invention relates to a new and distinct cultivar of *Sanguisorba officinalis* and will be referred to hereafter by its cultivar name, 'Tough Dream'. 'Tough Dream' represents a new Burnet, an herbaceous perennial grown for landscape use.

The inventor discovered the new cultivar, 'Tough Dream', as a chance seedling in a trial garden in September of 2018 in Rijnsburg, The Netherlands. The parentage is unknown.

Asexual propagation of the new cultivar was first accomplished by division in 2018 by the Inventor in Rijnsburg, The Netherlands. Asexual propagation by division has determined that the new cultivar is stable and reproduced true to type in successive generations.

SUMMARY OF THE INVENTION

The following traits have been repeatedly observed and represent the characteristics of the new cultivar. These attributes in combination distinguish 'Tough Dream' as a unique cultivar of *Sanguisorba*.

1. 'Tough Dream' exhibits strong branches.
2. 'Tough Dream' exhibits inflorescences and flowers that are small in size and deep burgundy-red in color
3. 'Tough Dream' exhibits sturdy and upright flowers.

'Tough Dream' can be most closely compared to *Sanguisorba officinalis* cultivars 'Big Dream', 'Red Dream', 'Fall Dream', and 'Sweet Dream'. 'Big Dream', 'Red Dream', 'Fall Dream', and 'Sweet Dream' are all similar to 'Tough Dream' in having upright plant habits and tall plant heights. 'Big Dream' differs from 'Tough Dream' in having inflorescences and stamen filaments that are grey-purple in color. 'Red Dream' differs from 'Tough Dream' in having a smaller plant size and filaments that are white in color. 'Fall Dream' differs from 'Tough Dream' in having larger inflorescences and weaker branches. 'Sweet Dream' differs from 'Tough Dream' in having flowers that are pink in color.

BRIEF DESCRIPTION OF THE DRAWINGS

The accompanying color photographs illustrate the overall appearance and distinct characteristics of the new *Sanguisorba*. The photographs were taken of a one-year-old plant of the new cultivar as field grown outdoors in Rijnsburg, The Netherlands and placed in a container for the photographs.

The photograph in FIG. 1 illustrates the overall habit and appearance of 'Tough Dream' in bloom.

Figure 1:
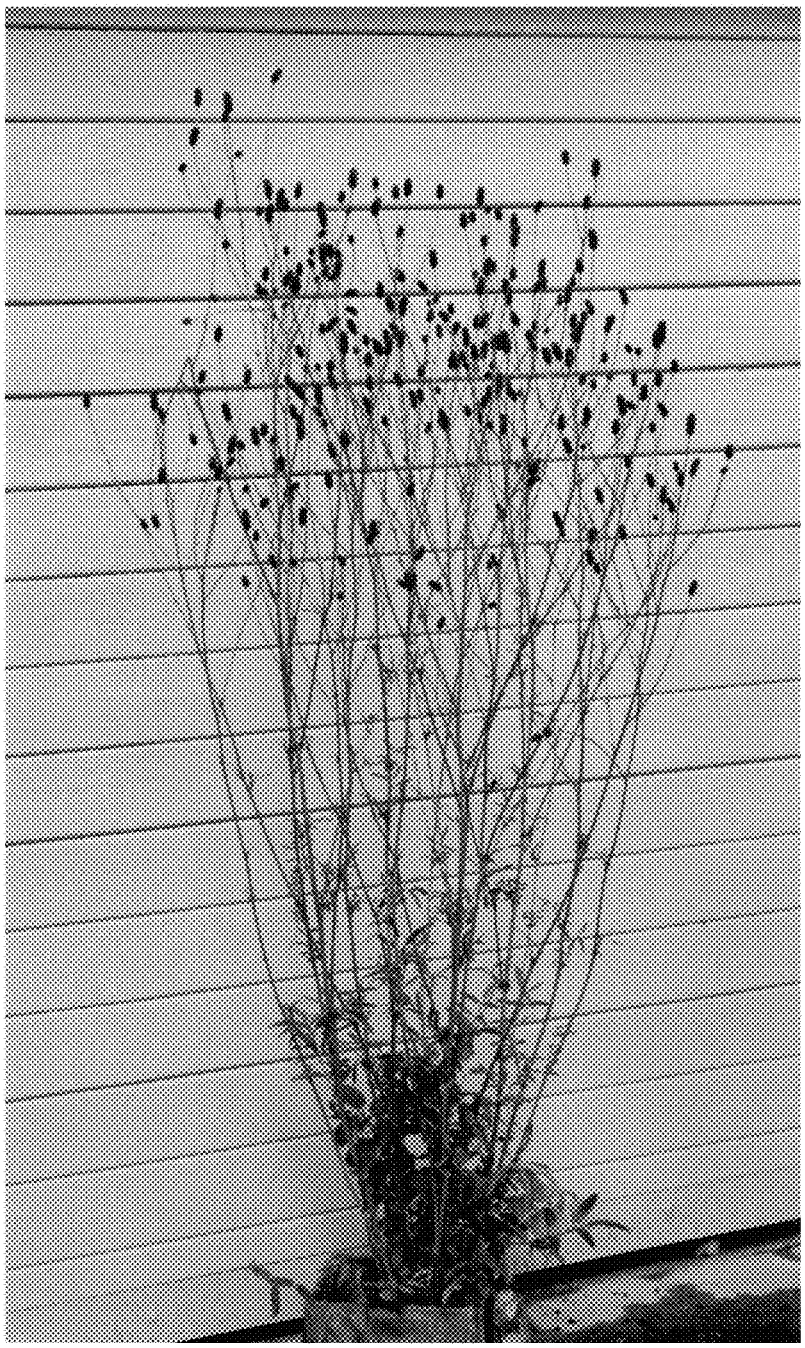
Figure 2:
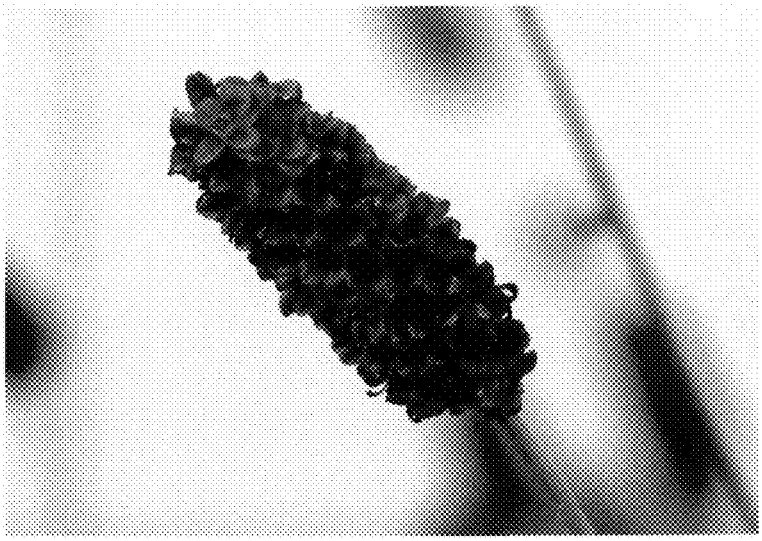

The photograph in FIG. 2 provides a close-up view of the inflorescences of 'Tough Dream'.

Figure 3:
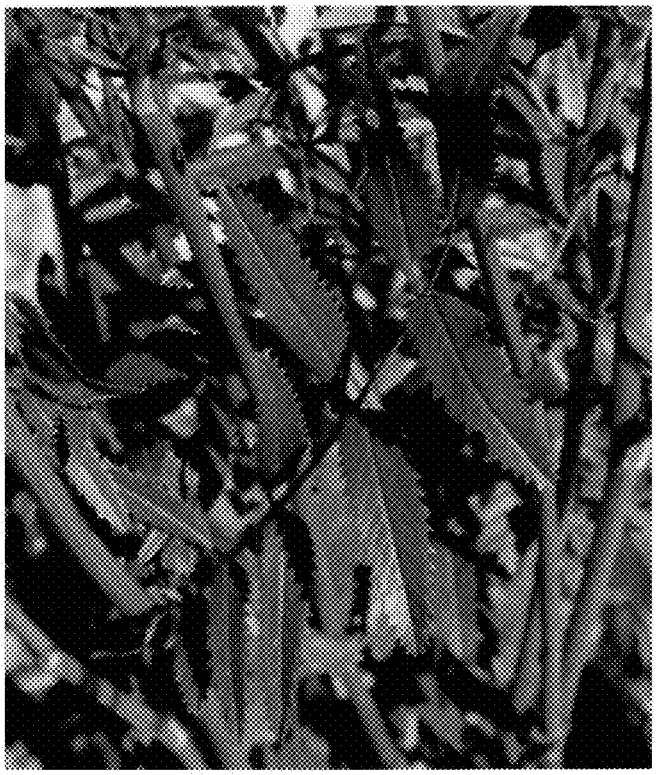

The photograph in FIG. 3 provides a close-up view of the foliage of 'Tough Dream'.

The colors in the photographs are as close as possible with the photographic and printing technology utilized and color values cited in the detailed botanical description accurately describe the colors of the new *Sanguisorba*.

DETAILED BOTANICAL DESCRIPTION

The following is a detailed description of one-year-old plants from a division of the new cultivar as field grown in Rijnsburg, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—September in The Netherlands.

*Plant shape.*—Oblong, upright.

*Plant habit.*—Herbaceous perennial.

*Height and spread.*—Average of 1.22 m in height from soil level to top of foliar plane, 1.72 m in height from soil level to top of floral plane, 83.5 cm in spread.

*Hardiness.*—At least in U.S.D.A. Zones 4 to 9.

*Diseases and pests.*—No susceptibility or resistance to diseases or pests has been observed.

*Root description.*—Moderately fibrous, very freely branched, smooth, glabrous with no root hairs, main roots are an average of 3 mm in diameter, 164C in color.

*Root development.*—A young plant rooted plant can be produced in 6 to 7 months.

*Propagation.*—Division.

*Growth rate.*—Vigorous.

Stem description:

*Shape.*—Round, moderately angled.

*Stem color.*—Young; 143B, mature; a blend of 143B and 144A.

*Stem size.*—Up to 1.2 m cm in length and 6 mm in diameter.

*Stem aspect.*—Average of 10° to vertical (varying between 0° and 20°).

*Stem surface.*—Slightly glossy.

*Internode length.*—Up to 10.9 cm.

*Branching.*—Average of 5 main branches and 30 lateral branches per plant.

Foliage description:

*Leaf shape.*—Narrow obovate.

*Leaf division.*—Compound, imparipinnate; an average of 11 leaflets per leaf (ranges from 13 leaflets on the lower leaves to 7 leaflets on the upper leaves).

*Leaf base.*—Truncate, upper stem leaflets attenuate.

*Leaf apex.*—Abruptly acute.

*Leaf aspect.*—Average of 40° to stem.

*Leaf arrangement.*—Alternate.

*Leaf size.*—Average of 35.8 cm in length (including petiole), 12.4 cm in width.

*Leaf attachment.*—Petiolate.

*Leaflet.*—Lanceolate to narrow oblong in shape, terminal leaflets; average of 6 cm in length, 2.6 cm in width, lateral leaflets; average of 5.9 cm in length and 2.5 cm in width, abruptly acute apex, truncate base.

*Leaflet venation.*—Pinnate, upper surface color 146C, lower surface 147C.

*Leaflet margins.*—Dentate to serrate.

*Leaflet surface.*—Both surfaces smooth and glabrous.

*Leaflet color.*—Young upper surface NN137A to NN137B, young lower surface a blend of 138A and 147B, mature upper surface NN137A, mature lower surface 147B.

*Rachis (petiole) and petiolule.*—Rachis (petiole); average of 27.8 cm in length, 2.25 mm in diameter, petiolule; average of 2 cm in length and 1 mm in diameter, slightly glossy, smooth and glabrous, strong, upper surface color 146B, rachis tinged 187B at the leaflet nodes, lower surface 146B, petiolules slightly lighter and 187B.

*Stipules.*—At the base of each leaf is a leafy stipule is present on each side, shaped falcate, average of 2.9 cm in length, 1.6 cm in width, both surfaces smooth and glabrous, margins dentate to serrate, top abruptly acute, upper side slightly glossy, color; NN137A, lower surface 147B, lower stem leaves; a leafy stipule is present on either side at the base of each petiolule, ovate to orbicular in shape, average of 1.2 cm in length, average of 1 cm in width, both surfaces smooth and glabrous, margins dentate to serrate, both surfaces slightly glossy, color; NN137A, lower surface 147B.

Inflorescence description:

*Type.*—Terminal spikes of numerous, densely packed flowers in elongated ovoid to oblong shaped inflorescence, determinate.

*Inflorescence size.*—Panicle; average of 40 cm in height, 34.8 cm in diameter, spike; 2.9 cm in height, 1.1 cm in diameter.

*Fragrance.*—Very faint and unpleasant.

*Flower lastingness.*—About 14 days, persistent.

*Flower quantity.*—Average of 115 flowers per spike, over 17,500 flowers and buds per plant.

*Flower aspect.*—Rotate, single, outward and freely flowering.

*Flower size.*—Average of 3.5 mm in height and diameter, 4 mm in depth.

*Peduncle.*—Average of 14.3 cm in length, 1.25 mm in diameter, held in an average of 0° to vertical, secondary 35° to vertical, strong, smooth and glabrous, slightly glossy, a blend of 144A and 146B in color.

*Bud description.*—Average of 2.5 mm in length and 1.5 mm in diameter, obovate in shape, smooth, glabrous, and matte surface, color; N186C, base 157A.

*Petals.*—Rotate, cruciform, average of 4, 1 row, unfused, 2 mm in length, 1.5 mm in width, broadly ovate in shape, tip is broadly acute and slightly recurved, broadly cuneate base, entire and undulate margins, both surfaces glabrous, slightly velvety and matte, color; when opening upper surface; N186A, margins 59C, when opening lower surface; N186A, margins 59B, when fully open upper and lower surface N186B, broadly margined 59B, veins N186B, both surfaces when fading N186B, broadly margined 59A.

*Calyx.*—Rotate, cruciform, average of 1.25 mm in length, 1 mm in diameter.

*Sepal.*—An average of 4 in 1 row, average of 1.25 mm in length and 0.75 mm in width, ovate in shape, bluntly acute tip, cuneate acute base, entire margins, both surfaces smooth and glabrous, color; when opening and fully open upper and lower surface 152D.

*Flower bracts.*—None.

Reproductive organs:

*Gynoecium.*—Pistil: 1, average of 2.5 mm in length, stigma is flattened and club-shaped, 0.3 mm in length and in diameter, 187B in color, style; average of 2.25 mm in length, 187B in color, base N187D, ovary; 143B in color.

*Androecium.*—Stamens; average of 4, filament; 1 mm in length, N186C in color, anthers; short, kidney-shaped, N186A in color, 0.5 mm in length and width, pollen; low in quantity, 23A in color.

*Fruit/seed.*—None observed.

It is claimed:

1. A new and distinct cultivar of *Sanguisorba* plant named 'Tough Dream' as herein illustrated and described.

* * * * *